United States Patent [19]

Nakamura

[11] Patent Number: 4,732,156

[45] Date of Patent: Mar. 22, 1988

[54] ULTRASONIC ENDOSCOPE

[75] Inventor: Takeaki Nakamura, Hino, Japan

[73] Assignee: Olympus Optical Co., Ltd., Japan

[21] Appl. No.: 871,470

[22] Filed: Jun. 6, 1986

[30] Foreign Application Priority Data

Jun. 21, 1985 [JP] Japan .................. 60-135318

[51] Int. Cl.[4] .................. A61B 10/00
[52] U.S. Cl. .................. 128/660; 128/4; 74/DIG. 4
[58] Field of Search .................. 128/660–663; 73/633; 74/DIG. 4

[56] References Cited

U.S. PATENT DOCUMENTS

| 3,085,407 | 4/1963 | Tomlinson | 74/DIG. 4 |
| 4,149,419 | 4/1979 | Cornell, Jr. et al. | 128/660 X |
| 4,375,818 | 3/1983 | Suwaki et al. | 128/660 |
| 4,442,842 | 4/1984 | Baba | 128/660 |
| 4,479,388 | 10/1984 | Matzuk | 128/660 X |
| 4,486,176 | 12/1984 | Tardieu et al. | 74/DIG. 4 X |
| 4,494,549 | 1/1985 | Namba et al. | 128/660 |
| 4,572,201 | 2/1986 | Kondo et al. | 128/4 X |

FOREIGN PATENT DOCUMENTS 0066185 12/1982 European Pat. Off. .......... 128/660

Primary Examiner—Francis J. Jaworski

[57] ABSTRACT

An ultrasonic endoscope includes an operation section and an insertion section extending therefrom. A driving member having a magnet is disposed in the distal end of the insertion section to be rotatable. The member is rotated by a motor through a transmission shaft. An ultrasonic scanning unit is removably attached to the distal end of the insertion section. The unit has a casing in which a scanning chamber filled with a liquid ultrasonic transmission medium is defined. A ultrasonic generator is disposed in the casing. A rotating mirror for reflecting the ultrasonic waves generated by the generator is rotatably arranged in the chamber. A driven member is rotatably arranged in the chamber and coupled to the mirror. The driven member has a magnet magnetically connected to the magnet of the driving member so that it rotates as the driving member rotates.

5 Claims, 3 Drawing Figures

ULTRASONIC ENDOSCOPE

BACKGROUND OF THE INVENTION

The present invention relates to an ultrasonic endoscope for an ultrasonic diagnosis on a desired region in the body cavity.

In general, ultrasonic endoscopes of this type comprise an operation section and an insertion section extending therefrom to be inserted into the body cavity. A distal member with a scanning chamber therein is attached to the distal end of the insertion section. The chamber is filled with a liquid ultrasonic transmission medium. Also, it contains an ultrasonic generator and a rotating mirror for reflecting, in a predetermined direction, ultrasonic waves generated from the generator. The mirror is rotated by a motor in the operation section. To this end, the motor is coupled to the mirror by a transmission shaft, such as a wire, which is passed through the insertion section.

The transmission shaft extends into the scanning chamber full of the liquid. In order to prevent the liquid from leaking from the chamber to the insertion section, the periphery of the shaft must be sealed by an O-ring or the like. In this case, however, that portion of the shaft sealed by the O-ring is subject to increased friction, requiring correspondingly greater driving torque. After long use, the O-ring would be deteriorated to have its sealing capability reduced. Consequently, the liquid in the scanning chamber would possibly leak from the scanning chamber.

SUMMARY OF THE INVENTION

The present invention has been contrived in consideration of these circumstances, and is intended to provide an ultrasonic endoscope which can reliably prevent an ultrasonic transmission medium from leaking from a scanning chamber, without the use of any special sealing means.

In order to achieve the above object, an ultrasonic endoscope according to the invention comprises an operation section; an insertion section having an axis and extending from the operation section, the insertion section being adapted to be inserted into the body cavity; a driving member disposed in the distal end portion of the insertion section to be rotatable around an axis parallel to the central axis of the insertion section; drive means for rotating the driving member; and an ultrasonic scanning unit attached to the distal end of the insertion section, the unit including a casing attached to the distal end of the insertion section and having an ultrasonic radiation window and a scanning chamber filled with a liquid ultrasonic transmission medium, an ultrasonic generator disposed in the scanning chamber and generating ultrasonic waves, and a rotary scanning mechanism for radiating the ultrasonic waves generated by the generator through the window and repeatedly deflecting the waves by a predetermined angle, the scanning mechanism including a driven member disposed opposite to the driving member in the scanning chamber to be rotatable around the same axis as the driving member, the driven member being magnetically connected to the driving member so that the driven member rotates as the driving member rotates.

BRIEF DESCRIPTION OF THE DRAWINGS

FIGS. 1 and 2 show an ultrasonic endoscope according to a first embodiment of the present invention, in which FIG. 1 is a side view of the endoscope and FIG. 2 is an enlarged sectional view of the distal end portion of an insertion section.

DETAILED DESCRIPTION OF THE PREFERRED EMBODIMENTS

Preferred embodiments of the present invention will now be described in detail with reference to the accompanying drawings.

Figure 1:
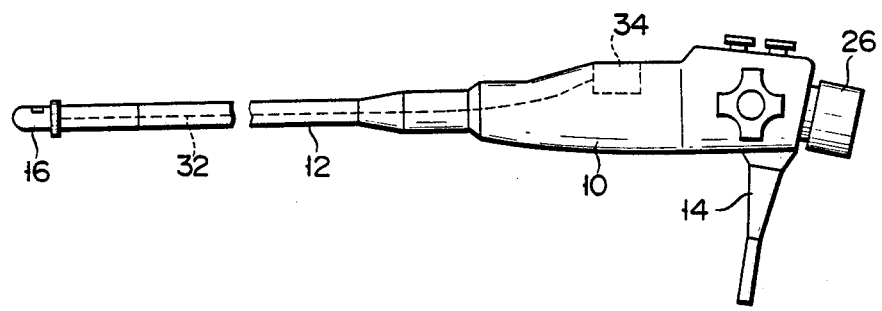

As shown in FIG. 1, an ultrasonic endoscope comprises operation section 10, insertion section 12, and universal cord 14. Section 12 and cord 14 both extend from section 10. Ultrasonic scanning unit 16, as mentioned later, is attached to the distal end of section 12.

Figure 2:
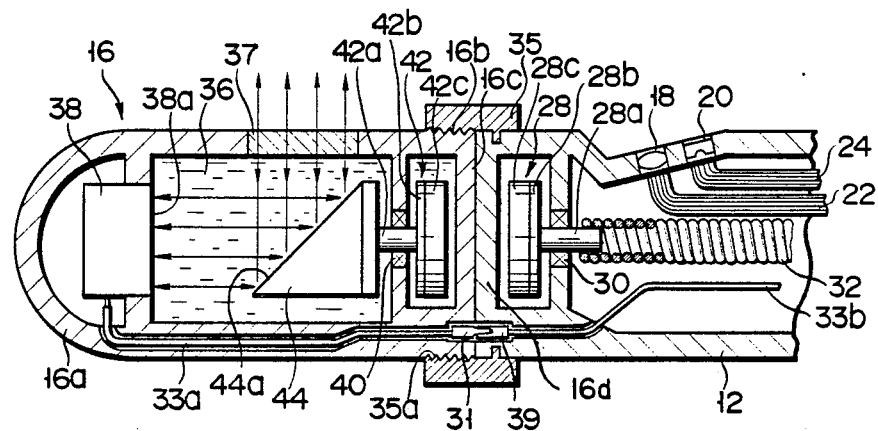

As shown in FIG. 2, illumination window 18 and observation window 20 are arranged on the outer peripheral surface of the distal end portion of insertion section 12. One end of light guide 22 is fixed to window 18. The light guide extends to the distal end of universal cord 14 through sections 12 and 10 and the cord. One end of image guide 24 is connected to window 20. The image guide extends through sections 12 and 10 to eyepiece portion 26 provided at operation section 10. Driving member 28, supported by bearing 30 for rotation around the axis of insertion section 12, is disposed inside the distal end portion of section 12. Member 28 includes base 28b with pivot 28a and disk-shaped permanent magnet 28c fixed to the base and positioned coaxial with the pivot. Pivot 28a is supported by bearing 30, and magnet 28c adjacently faces the distal end face of insertion section 12. Transmission shaft 32, formed of a closely-wound coil, is rotatably passed through the insertion section. One end of shaft 32 is connected to pivot 28a of driving member 28, and the other end to a drive shaft (not shown) of motor 34 in operation section 10. Thus, member 28 is rotated by motor 34 with the aid of shaft 32. Coupling ring 35 is rotatably mounted on the outer peripheral surface of the distal end portion of insertion section 12. It projects forward from the distal end of section 12, and is formed with threaded portion 35a on its inner periphery.

Ultrasonic scanning unit 16 includes substantially cylindrical casing 16a closed at both ends and having threaded portion 16b on the outer peripheral surface of its proximal end portion. Unit 16 can be removably attached to the distal end of insertion section 12 by causing portion 16b to engage threaded portion 35a of coupling ring 35. When unit 16 is mounted on section 12, proximal end wall 16c of casing 16a is closely in contact with the distal end face of end-wall 16d of the insertion section. Closed scanning chamber 36 is defined in casing 16a. It is filled with a liquid ultrasonic transmission medium isolated from the insertion section. An aperture is cut in the peripheral wall of casing 16a, connecting chamber 36 and the outside of the casing. Ultrasonic radiation window 37 is fitted in the aperture. Ultrasonic vibrator 38 is disposed inside the distal end portion of casing 16a. It has ultrasonic emitting/receiving surface 38a which intersects the axis of insertion section 12 at right angles and constitutes one side face of scanning chamber 36. Signal cable 33a is buried in the peripheral wall of casing 16a. One end of cable 33a is connected to vibrator 38, and the other end to connector 31 provided in proximal end wall 16c of casing 16a. Signal cable 33b is passed through insertion section 12. One end of cable 33b is connected to socket 39 provided at the distal end of the insertion section. Cable 33b extends through operation section 10 and universal cord 14, and is connected to an image processing apparatus and display unit (not shown). When ultrasonic scanning unit 16 is attached to insertion section 12, connector 31 is connected to socket 39, so that vibrator 38 is electrically connected to the image processing apparatus and display unit.

Driven member 42 is disposed in scanning chamber 36, located close to the proximal end wall of casing 16a. It is supported by bearing 40 and can rotate around the axis of insertion section 12. The driven member includes base 42b, having pivot 42a supported by bearing 40, and disk-shaped permanent magnet 42c fixed to the base. Magnet 42c, which is coaxial with section 12, adjacently faces the proximal end wall of casing 16a. Thus, magnets 28c and 42c of driving member 28 and driven member 42 face, with the distal end wall of insertion section 12 and proximal end wall 16c of casing 16a between them. In consequence, these two magnets are connected magnetically. When member 28 is rotated, member 42 rotates correspondingly.

Rotating mirror 44 is disposed in scanning chamber 36. It is located between ultrasonic vibrator 38 and driven member 42, and connected to pivot 42a of member 42. The position of driven member 44 relative to casing 16a can be determined by any suitable means, as will occur to those skilled in the art based on the teaching of this disclosure. Thus, it can rotate in one with the driven member. Mirror 44 has reflecting surface 44a which is inclined at 45° to the axis of rotation of member 42, i.e., to the axis of insertion section 12. Surface 44a reflects ultrasonic waves generated by vibrator 38 so that the waves are radiated through radiation window 37. As mirror 44 rotates, the waves reflected by surface 44a are deflected around the rotation axis of the mirror. The ultrasonic waves radiated through window 37 strike against some tissue in the body cavity, are reflected by the tissue, and are applied back into scanning chamber 36 through window 37. They are reflected by reflecting surface 44a and received by emitting/receiving surface 38a of vibrator 38.

To operate the ultrasonic endoscope to perform an ultrasonic diagnosis, insertion section 12 is inserted into a desired internal organ, and radiation window 37 is directed toward a region to be examined. Then, motor 34 is started, so that driving member 28 is rotated by transmission shaft 32. As a result, driven member 42, which is magnetically coupled to member 28, and rotating mirror 44 rotate together. The rotating speed of motor 34 is adjusted according to the kind of the organ as an object of diagnosis. In this state, ultrasonic vibrator 38 is actuated so that ultrasonic waves are generated from emitting/receiving surface 38a. The waves are reflected by reflecting surface 44a of rotating mirror 44 and fed through radiation window 37 for scanning the organ. The reflected waves from the organ are introduced into scanning chamber 36 through window 37, reflected by surface 44a, and received by surface 38a of vibrator 38. The waves are converted into an electrical signal, which is fed through signal cables 33a and 33b to the image processing apparatus and processed thereby. The processed signal forms an image on the display unit.

According to the ultrasonic endoscope constructed in this manner, driven member 42, which is disposed in ultrasonic scanning unit 16 and coupled to rotating mirror 44, is magnetically connected to driving member 28 which is provided in insertion section 12. Therefore, member 42 and mirror 44 can be rotated remotely from the insertion section by rotating the driving member. Thus, transmission shaft 32 need not be coupled to mirror 44 through scanning chamber 36, and the drive system provided in chamber 36 needs no sealing means. In consequence, chamber 36 has an improved sealing effect, and the drive system is free from output loss due to the use of sealing means.

A drive mechanism in ultrasonic scanning unit 16, including rotating mirror 44 and driven member 42, is not mechanically connected to the drive system in insertion section 12, which includes driving member 28 and transmission shaft 32. Accordingly, unit 16 can easily be removed from the section 12 by only loosening coupling ring 35. Thus, unit 16 may readily be replaced with any other unit including an ultrasonic vibrator with a different oscillation frequency or a rotating mirror whose reflecting surface 44a has a varied tilt angle. The direction of ultrasonic radiation can be changed by varying the tilt angle of surface 44a.

Figure 3:
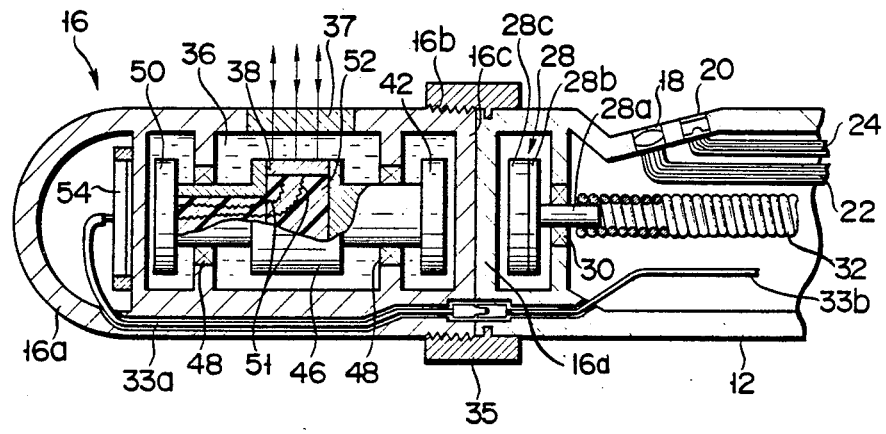
FIG. 3 is an enlarged sectional view of the distal end portion of an insertion section of an ultrasonic endoscope according to a second embodiment of the invention.

FIG. 3 shows an ultrasonic endoscope according to a second embodiment of the present invention. In this embodiment, like reference numerals are used to designate like portions as in the first embodiment.

Cylindrical rotor 46 is disposed in scanning chamber 36 of casing 16a so as to be coaxial with insertion section 12. It is supported by a pair of bearings 48 for rotation on its axis. Ultrasonic vibrator 38 is fixed to that portion of the peripheral wall of rotor 46 which corresponds to radiation window 37. Disk-shaped driven member 42, formed of a permanent magnet, is coaxially fixed to that end of rotor 46 on the side of insertion section 12, adjacently facing proximal end wall 16c of casing 16a. Thus, driven member 42 is magnetically coupled to driving member 28 provided in section 12. Disk-shaped first signal transmission member 50, having a coil buried therein, is coaxially fixed to the other end of rotor 46. The coil buried in member 50 is electrically connected to ultrasonic vibrator 38 by means of lead wires 51 which extend through rotor 46. The rotor is filled with damper material 52, e.g., elastic resin, for absorbing undesired ultrasonic waves. Disk-shaped second signal transmission member 54, also having a coil buried therein, is disposed in casing 16a, located outside scanning chamber 36. Member 54 is opposed to first transmission member 50. The coil in member 54 is connected to the image processing apparatus and display unit (not shown) by signal cables 33a and 33b.

When driving member 23 is rotated by motor 34 (FIG. 1), driven member 42 and rotor 46 are rotated. As a result, ultrasonic waves emitted from ultrasonic vibrator 38 are radiated from casing 16a through radiation window 37, for scanning along the circumference of a circle around the rotation axis of rotor 46. The waves reflected by an internal organ are fed through window 37 into scanning chamber 36 and received by vibrator 38. The received waves are converted into an electrical signal, which is delivered to the coil of first transmission member 50 through lead wires 51. The electrical signal is converted into a magnetic signal by the coil, and delivered to second transmission member 54. Then, the magnetic signal is converted again into an electrical signal by the coil of member 54, and fed through signal cables 33a and 33b to the signal processing apparatus.

With the arrangement described above, the second embodiment provides the same functions and effects of the first embodiment.

It is to be understood that the present invention is not limited to the embodiments described above. Various changes and modifications may be effected by one skilled in the art, without departing from the scope or spirit of the invention. Although both the driving and driven members are formed of a magnet in the first and second embodiments, only one of them must be made of a magnet. The other may be formed of either a magnet or a magnetic substance.

What is claimed is:

1. An ultrasonic endoscope comprising:
   an operation section;
   an insertion section having a longitudinal axis and extending from the operation section, said insertion section being adapted to be inserted into a body cavity;
   a driving member mounted in a distal end portion of the insertion section to be rotatable with respect to said insertion section around an axis parallel to the longitudinal axis of the insertion section, said insertion section being closed by a distal end wall located adjacent to said driving member so that said driving member can be enclosed in said insertion section;
   drive means for rotating the driving member; and
   an ultrasonic scanning unit attached to the distal end of the insertion section, said unit including a casing having an ultrasonic radiation window and a scanning chamber filled with a liquid ultrasonic transmission medium, said scanning chamber including a scanning chamber wall adapted to be located adjacent to said insertion section end wall, an ultrasonic generator disposed in the scanning chamber and generating ultrasonic waves, and a rotary scanning means for radiating the ultrasonic waves generated by the generator through the window and repeatedly deflecting the waves by a predetermined angle, said scanning means including a driven member enclosed within said scanning chamber and mounted to be rotatable with respect to said casing, said driven member being fluidically isolated from said driving member by said scanning chamber wall and said insertion section distal end wall and being coupled to said driving member by a magnetic coupling, said driven member being disposed in the scanning chamber to be opposite to said driving member so as to be rotatable around the same axis as the driving member while being rotatable with respect thereto, the magnetic coupling between said driven member and said driving member causing said driven member to rotate as the driving member rotates; and
   connecting means for detachably connecting said scanning unit to said insertion section with said insertion section end wall in abutting contact with said scanning chamber wall, whereby said scanning chamber and said insertion section are fluidically isolated from each other when said scanning unit is attached to said insertion section and said scanning chamber can remain fluidically closed when said scanning unit is detached from said insertion section.

2. The ultrasonic endoscope according to claim 1, wherein at least one of said driving and driven members includes a magnet, and the other includes another magnet or a magnetic substance magnetically connected to the magnet.

3. The ultrasonic endoscope according to claim 2, wherein said rotary scanning means includes a rotating mirror coupled to the driven member and adapted to rotate in unison therewith, said mirror having a reflecting surface for reflecting the ultrasonic waves generated by the ultrasonic generator to radiate them from the casing through the radiation window, and for reflecting the reflected waves introduced into the scanning chamber through the radiation window toward the ultrasonic generator.

4. The ultrasonic endoscope according to claim 2, wherein said rotary scanning means includes a rotor coupled to the driven member and adapted to rotate in unison therewith, and said ultrasonic generator is fixed to the rotor so as to face the radiation window.

5. The ultrasonic endoscope according to claim 4, wherein said ultrasonic scanning unit includes a first signal transmission means fixed to the rotor and electrically connected to the ultrasonic generator, for converting an electrical signal delivered from the ultrasonic generator into a magnetic signal, and a second signal transmission means disposed in the casing and located outside the scanning chamber and opposite to the first signal transmission means, for receiving the magnetic signal from the first signal transmission means and converting it into an electrical signal.

* * * * *